US010722723B2

(12) United States Patent
Schmidt et al.

(10) Patent No.: US 10,722,723 B2
(45) Date of Patent: Jul. 28, 2020

(54) DELIVERY DEVICES AND METHODS FOR LEADLESS CARDIAC DEVICES

(71) Applicant: Cardiac Pacemakers, Inc., St. Paul, MN (US)

(72) Inventors: Brian L. Schmidt, White Bear Lake, MN (US); Benjamin J. Haasl, Forest Lake, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 809 days.

(21) Appl. No.: 14/452,617

(22) Filed: Aug. 6, 2014

(65) Prior Publication Data

US 2015/0051613 A1    Feb. 19, 2015

Related U.S. Application Data

(60) Provisional application No. 61/866,898, filed on Aug. 16, 2013.

(51) Int. Cl.
*A61M 25/00*  (2006.01)
*A61N 1/375*  (2006.01)

(52) U.S. Cl.
CPC .................. *A61N 1/3756* (2013.01)

(58) Field of Classification Search
CPC .............. A61N 1/3756; A61N 1/37205; A61N 1/0573; A61N 1/362; A61N 1/057; A61N 1/357; A61N 1/056; A61N 1/059; A61N 1/05; A61N 1/37229; A61N 1/0551; A61N 1/0553; A61N 1/0587; A61N 1/0558; A61N 1/0568; A61N 1/0575; A61N 1/0597;

(Continued)

(56) References Cited

U.S. PATENT DOCUMENTS

| 721,869 A | 3/1903 | Dunning |
| 3,717,151 A | 2/1973 | Collett |

(Continued)

FOREIGN PATENT DOCUMENTS

| CA | 1003904 A1 | 1/1977 |
| DE | 2053919 A1 | 5/1972 |

(Continued)

OTHER PUBLICATIONS

Spickler, et al. "Totally Self-Contained Intracardiac Pacemaker" J. Electrocardiology, vol. 3, Nos. 3 & 4, pp. 325-331 (1970).

*Primary Examiner* — Ryan J. Severson
*Assistant Examiner* — Socrates L Boutsikaris
(74) *Attorney, Agent, or Firm* — Seager, Tufte & Wickhem LLP (57) ABSTRACT

Delivery devices, systems, and methods for delivering an implantable leadless pacing device having an outer peripheral surface are disclosed. An example delivery device may include a proximal section including a distal end, and a distal holding section extending distally of a distal end of the proximal section. The distal holding section defines a cavity therein for receiving the implantable leadless pacing device, and may be configured to apply a holding force to the implantable leadless pacing device. In some cases, the distal holding section may be configured to apply a compressive force to the outer peripheral surface of the leadless pacing device when the leadless pacing device is disposed in the cavity.

20 Claims, 5 Drawing Sheets

(58) Field of Classification Search
CPC .... A61N 1/3605; A61N 1/3627; A61N 1/365; A61N 2001/058; A61N 2001/0578; A61N 2001/0585; A61F 2/966; A61F 2002/011; A61M 2025/0024; A61M 2025/0081; A61M 2025/0681; A61M 25/0074; A61B 17/3468; A61B 17/3439; A61B 2017/1205
USPC ........... 606/129, 108; 607/127, 126, 36, 128
See application file for complete search history.

(56) References Cited

U.S. PATENT DOCUMENTS

| | | |
|---|---|---|
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,743,240 B2 | 6/2004 | Smith et al. |
| 6,755,812 B2 | 6/2004 | Peterson et al. |
| 6,909,920 B2 | 6/2005 | Lokhoff et al. |
| 6,944,507 B2 | 9/2005 | Froberg et al. |
| 6,953,454 B2 | 10/2005 | Peterson et al. |
| 7,027,876 B2 | 4/2006 | Casavant et al. |
| 7,082,335 B2 | 7/2006 | Klein et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Rutten et al. |
| 7,920,928 B1 | 4/2011 | Yang et al. |
| 7,993,351 B2 | 8/2011 | Worley et al. |
| 8,010,209 B2 | 8/2011 | Jacobson |

(56) References Cited

U.S. PATENT DOCUMENTS

| | | |
|---|---|---|
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 2002/0077556 A1 | 6/2002 | Schwartz |
| 2003/0004537 A1* | 1/2003 | Boyle ............... A61F 2/013 606/200 |
| 2004/0176797 A1 | 9/2004 | Opolski |
| 2005/0080430 A1* | 4/2005 | Wright, Jr. ....... A61B 17/22031 606/108 |
| 2005/0090890 A1 | 4/2005 | Wu et al. |
| 2005/0267555 A1 | 12/2005 | Marnfeldt et al. |
| 2006/0247753 A1 | 11/2006 | Wenger et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2009/0082828 A1 | 3/2009 | Ostroff |
| 2009/0143853 A1* | 6/2009 | Morris ............... A61F 2/93 623/1.16 |
| 2009/0281605 A1 | 11/2009 | Marnfeldt et al. |
| 2010/0198288 A1 | 8/2010 | Ostroff |
| 2011/0034939 A1 | 2/2011 | Kveen et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1* | 1/2013 | Berthiaume ............ A61F 2/966 604/529 |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Medtronic |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |

FOREIGN PATENT DOCUMENTS

| | | |
|---|---|---|
| EP | 779080 B1 | 5/2003 |
| JP | 05245215 A | 9/1993 |
| WO | 03032807 A2 | 4/2003 |
| WO | 2009039400 A1 | 3/2009 |
| WO | 2012092067 A1 | 7/2012 |
| WO | 2012092074 A1 | 7/2012 |

* cited by examiner

DELIVERY DEVICES AND METHODS FOR LEADLESS CARDIAC DEVICES

CROSS-REFERENCES TO RELATED APPLICATIONS

This application claims the benefit of U.S. Provisional Application No. 61/866,898 filed Aug. 16, 2013, the complete disclosure of which is herein incorporated by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery system, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices. An example medical device includes a delivery device for delivering an implantable leadless pacing device having an outer peripheral surface. The delivery device may include a proximal section including a distal end, and a distal holding section extending distally of a distal end of the proximal section. The distal holding section defines a cavity therein for receiving the implantable leadless pacing device, and may be configured to apply a holding force to the implantable leadless pacing device. In some cases, the distal holding section may be configured to apply a compressive force to the outer peripheral surface of the leadless pacing device when the leadless pacing device is disposed in the cavity. In some embodiments, the distal holding section includes an annular wall having an inner surface defining the cavity, and wherein the inner surface presses circumferentially against the outer peripheral surface of the leadless pacing device when the leadless pacing device is disposed in the cavity. In some cases, the distal holding section comprises a heat shrink material that applies the compressive force to the outer peripheral surface of the leadless pacing device. In some cases, the distal holding section comprises a resilient material that applies the compressive force to the outer peripheral surface of the leadless pacing device, for example a resilient material that elastically deforms when the leadless pacing device is disposed in the cavity. In other cases, the distal holding section may include a material that plastically deforms when the leadless pacing device is disposed in the cavity.

In some embodiments, the cavity of the distal holding section comprises an inner diameter, and the inner diameter is the same as or less than an outer diameter of the leadless pacing device. For example, where the inner diameter is less than an outer diameter of the leadless pacing device, and the holding section may be expandable such that the inner diameter expands when the leadless pacing device is disposed in the cavity.

In some situations, the cavity of the distal holding section comprises a distal portion that has an inner diameter that is less than the outer diameter of the leadless pacing device, and the distal portion may be expandable such that the inner diameter of the distal portion will expand as the leadless pacing device is delivered there through. In some situations, the cavity of the distal holding section includes a proximal section having a first inner diameter that is the same as the an outer diameter of the leadless pacing device, and a distal section that has a second inner diameter that is less than the outer diameter of the leadless pacing device.

In some embodiments, the distal holding section includes an annular wall having an inner surface defining the cavity, the inner surface configured to engage the outer peripheral surface of the leadless pacing device while being free of any gap between the inner surface of the annular wall and outer surface of the leadless pacing device.

In some embodiments, the compressive force applied by the distal holding section to the outer peripheral surface of the leadless pacing device provides circumferential frictional engagement between the distal holding section and the leadless pacing device. In some embodiments, the distal holding section slidably receives the implantable leadless pacing device, which in some cases is a non-expandable, implantable leadless pacing device, for example, an implantable leadless pacing device including a non-expandable housing.

Some embodiments relate to an implantable leadless pacing device system including a delivery device including elements or configurations set forth above, or disclosed herein; and an implantable leadless pacing device disposed within the cavity of the distal holding section of the delivery device.

Some other embodiments relate to methods for delivering an implantable leadless pacing device. The methods may include delivering the implantable leadless pacing device into the heart of a patient using a delivery system or delivery device including elements or configurations set forth above, or disclosed herein.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the invention.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. It can be readily appreciated that the implantation of a leadless pacing device within a beating heart could become dislodged as the heart functions. Accordingly, it may be desirable for a leadless pacing device to include one or more anchoring mechanism or member to help securing the pacing device to the heart.

Figure 1:
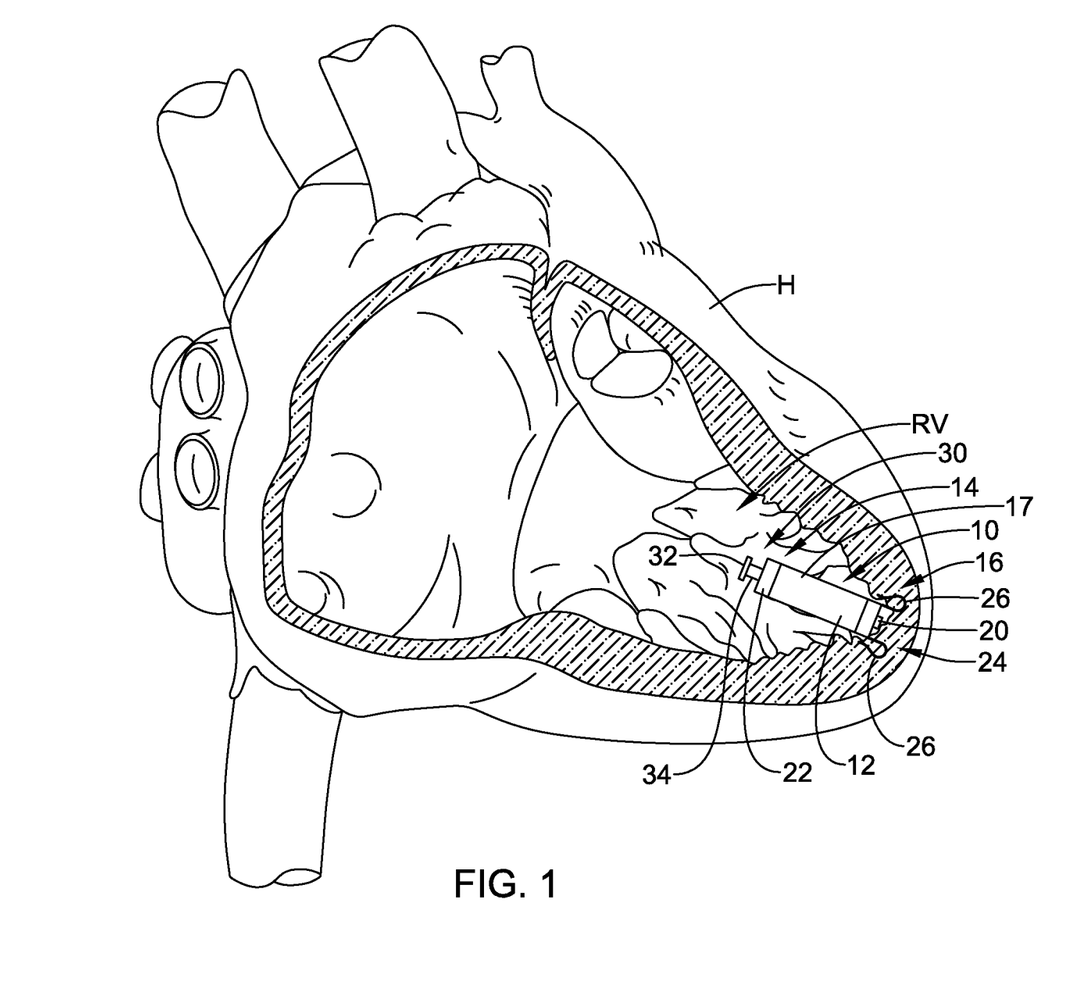
FIG. 1 is a plan view of an example leadless pacing device implanted within a heart.

FIG. 1 illustrates an example implantable leadless cardiac pacing device 10 (e.g., a leadless pacemaker) is illustrated implanted in a chamber of a heart H, such as the right ventricle RV. The implantable device 10 may include a shell or housing 12 having a proximal end 14, a distal end 16 and an outer peripheral surface 17. The housing 12 may be a non-expandable housing. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along proximal end 14 may be free of insulation so as to define second electrode 22. The electrodes 20, 22 may be sensing and/or pacing electrodes to provide electro-therapy and/or sensing capabilities. The first electrode 20 may be capable of being positioned against or otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10. The docking member 30 may be configured to facilitate delivery of the implantable device 10 to the intracardiac site and/or retrieval of the implantable device 10 from the intracardiac site.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. It may be desirable to provide the delivery system with certain features that may allow for easier or better control for navigation or delivery purposes, and securement of the device 10 with the delivery device or system until deployment is desired. For example, delivery devices with a smaller delivery profile may be desired. It may also be desired to provide for delivery devices that securely hold or maintain the device 10 with, in, or on the delivery device during navigation or positioning of the device 10 to or at the target cite prior to deployment of the device 10, and then allows deployment of the device 10 when desired.

Figure 2:
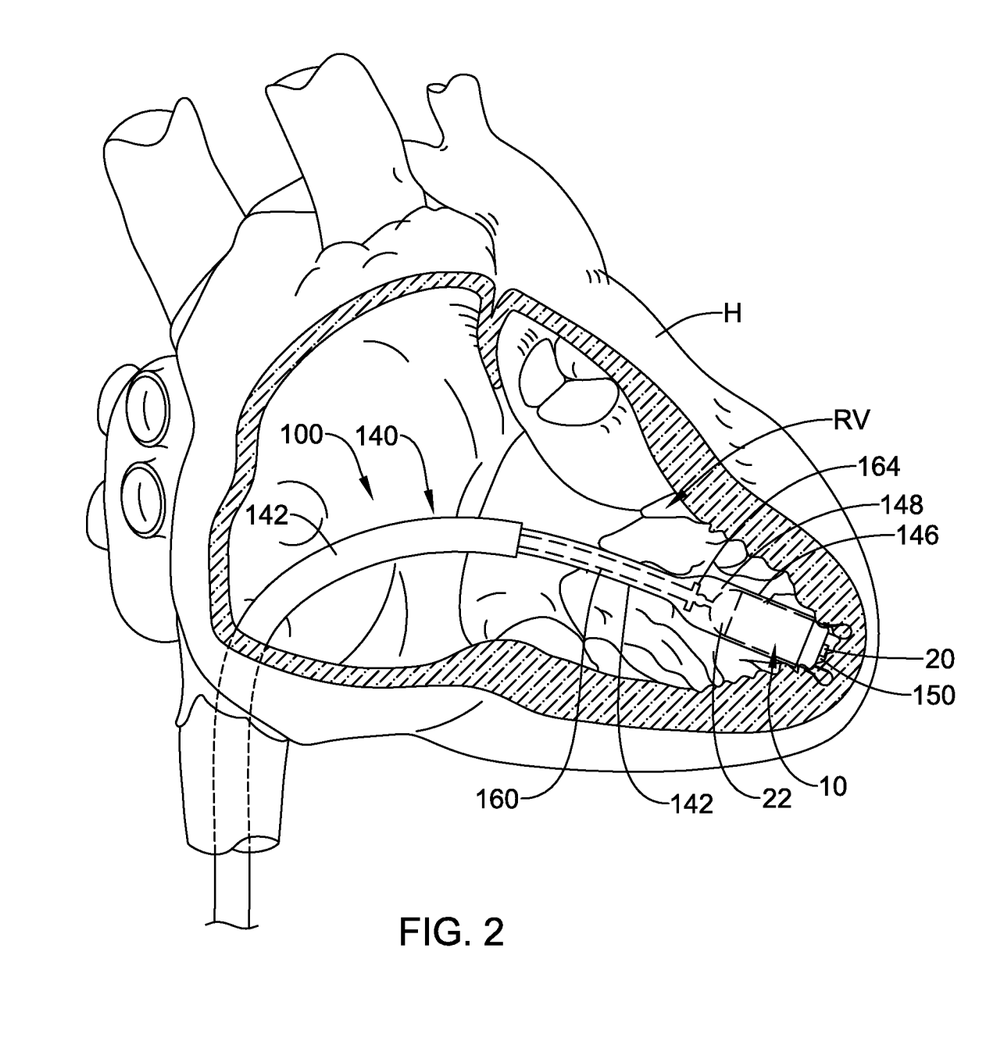
FIG. 2 is a plan view of an example delivery device delivering an implantable leadless cardiac pacing device to the heart of a patient.

FIG. 2 illustrates an example embodiment of a delivery device 100, such as a catheter, that may be used to deliver the device 10 to a target anatomy, for example, a portion of the right ventricle RV near the apex of the heart H as shown. Delivery device 100 may include a proximal section 140, such as a proximal shaft or tubular member 142, and a distal section and/or holding section 146, attached to the distal end of the proximal section 140. The distal holding section 146 may extend distally of a distal end of the proximal section 140. In some embodiments, the proximal section 140 may include at least a section thereof that has an outer diameter that is less than the outer diameter of at least a portion of the holding section 146. In some cases, the distal holding section comprises a polymer that is softer than that of the proximal section. For example, the distal holding section may comprise a polymer the having a durometer less than that of at least a portion of the proximal section.

The distal holding section 146 may be configured to receive the implantable device 10 therein. For example, the holding section 146 may define a cavity 148 for slidably receiving the implantable device 10, and may include a distal opening 150 for slidable insertion and/or extraction of the implantable device 10 into and/or out of the cavity 148. As will be discussed in more detail below, the distal holding section 146 may be configured to secure or hold the implantable device 10 therein until deployment is desired.

A push member 160 may be disposed (e.g., slidably disposed) within a lumen of the delivery device 100, for example through a lumen of the proximal section 140 of shaft 142. The push member 160 may be engaged by a user near the proximal end of the delivery device 100, and extend through a lumen in the delivery device 100, through the proximal section 140 and into the distal holding section 146. A distal portion 164 of the push member 160 may be capable of engaging the device 10, and the push member 160 may be used to "push" device 10 out from distal holding section 146 so as to deploy and anchor device 10 within a target region (e.g., a region of the heart such as the right ventricle).

As indicated above, the distal holding section 146 may be configured to secure or hold the implantable device 10 therein until deployment is desired. For example, referring to FIG. 3, the distal holding section 146 may be configured in such a way as to provide a holding force to maintain the implantable device 10 when the implantable device 10 is disposed therein. For example, the distal holding section 146 may be configured to provide a holding force between the outer peripheral surface 17 of the implantable device 10 and at least a portion of the distal holding section 146 when the implantable device 10 is disposed therein.

Figure 3:
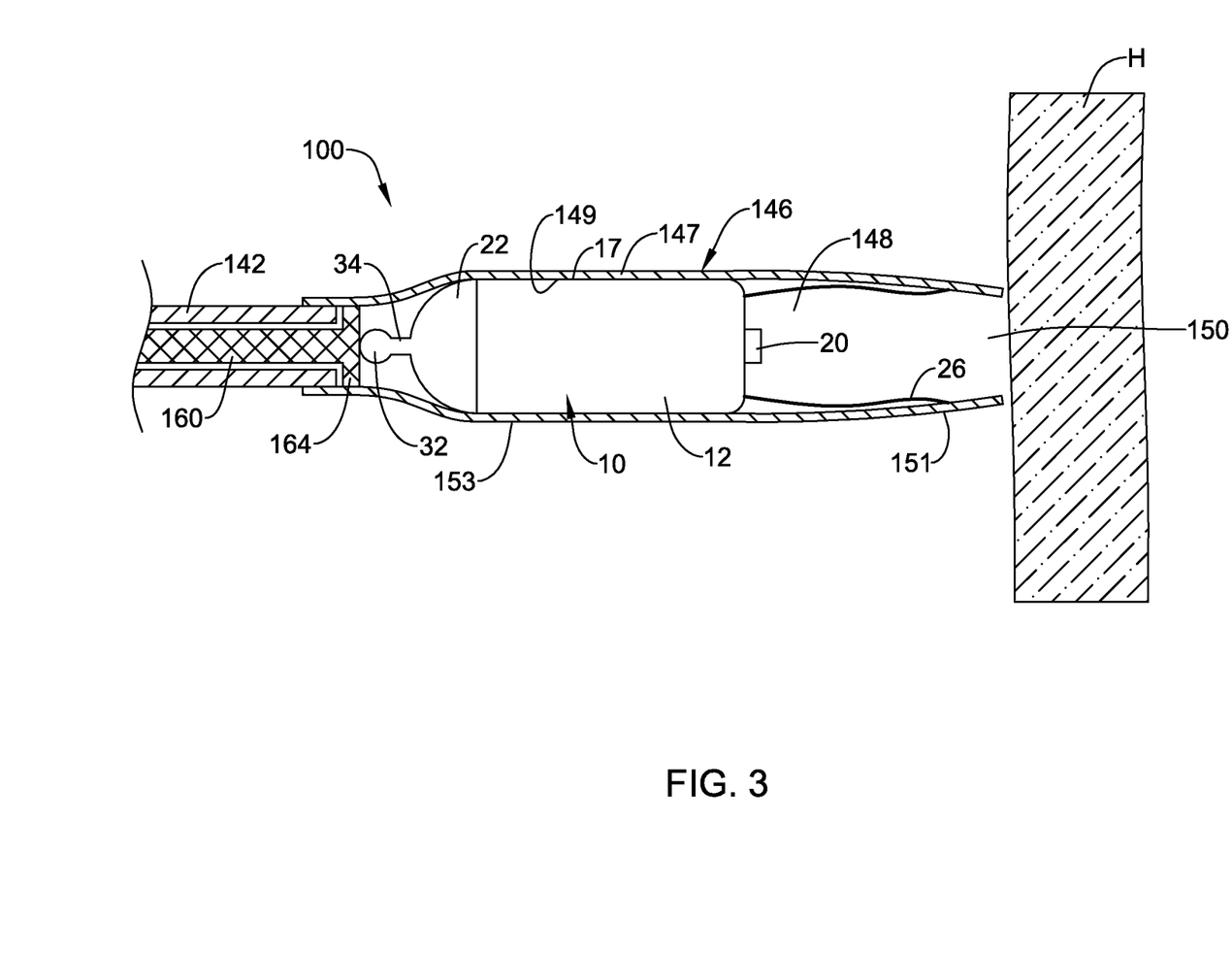
FIG. 3 is a partial cross-sectional side view of the distal portion of the delivery device of FIG. 2, showing the implantable leadless cardiac pacing device disposed therein prior to deployment.

In some embodiments, the distal holding section 146 may be configured to apply a compressive force to the outer peripheral surface 17 of the leadless pacing device 10 when the leadless pacing device is disposed in the cavity 148. This compressive force may act as a holding force to aid in selectively maintaining the implantable device 10 within the cavity 148. For example, in the embodiment shown, the distal holding section 146 may include an annular wall 147 having an inner surface 149 defining the cavity 148. The distal holding section 146 may be configured such that the inner surface 149 applies a compressive force against the outer peripheral surface 17 of the leadless pacing device 10 when the leadless pacing device is disposed in the cavity 148. For example, distal holding section 146 may include structure or materials that biases or predisposes at least a portion of the inner surface 149 to apply a compressive force against the outer surface 17. In some aspects, the inner surface 149 may be configured to grasp, grip, hug, squeeze, or clinch the outer peripheral surface 17 of the leadless pacing device 10. The compressive force may be circumferential about the housing 12 along at least a portion of the length of the housing 12. For example, in some cases, there is no gap or opening between the inner surface 149 and the outer peripheral surface 17 around the entire circumference of the leadless pacing device 10 along at least a portion of the length of the housing 12. In some cases, the compressive force may provide enhanced circumferential frictional engagement between the surfaces 149 and 17.

A number of ways are contemplated to generate such a holding force.

For example, in some embodiments, the distal holding section 146 may include or be made of a shrinkable material, such as a heat shrink material or the like. In some such embodiments, the leadless pacing device 10 may be disposed within the cavity 148, and heat or other activation mechanism may be applied to the shrink material such that at least a portion of the distal holding section 146 shrinks around at least a portion of the outer peripheral surface 17 of the leadless pacing device 10. As such, at least a portion of the inner surface 149 of the distal holding section 146 applies the compressive force to the outer peripheral surface 17 of the leadless pacing device.

In some embodiments, the distal holding section 146 may include or be made of a resilient or elastic material or structure that may apply a compressive force to the outer peripheral surface 17 of the leadless pacing device 10 when disposed therein. Such resilient or elastic material or structures may or may not be shrinkable materials. For example, distal holding section 146 may be made of resilient or elastic material or structure, and may be dimensioned such that in a relaxed state, the cavity 148 has an inner diameter that is the same as or smaller than an outer diameter of the leadless pacing device 10, for example the outer diameter of the housing 12 of the leadless pacing device 10. The leadless pacing device 10 is disposed within the cavity 148, thereby stretching or elastically deforming the distal holding section 146 to receive the leadless pacing device 10. Due to the dimensional differences, and the resilient or elastic properties of the distal holding section 146, a compressive force is applied to the outer peripheral surface 17 of the leadless pacing device 10. Some examples of such elastic material include elastic polymers, metals, or the like or combinations thereof. In a similar manner, some examples of structures that may be incorporated into the distal holding section 146 that may provide resilient or elastic properties thereto include an elastic coil, braid, or other similar structures.

In some other embodiments, the distal holding section 146 may include or be made of a non-resilient or plastically deformable material or structure that applies a holding force to the outer peripheral surface 17 of the leadless pacing device 10. Such non-resilient or plastically deformable material or structure may or may not be shrinkable materials. For example, distal holding section 146 made of non-resilient or plastically deformable material or structure, and may be dimensioned such that the cavity 148 has an inner diameter that is substantially the same as or less than the outer diameter of the leadless pacing device 10. When the leadless pacing device 10 is inserted into the cavity 148 of the distal holding section 146, the distal holding section may plastically deform tightly around the leadless pacing device 10 (in the case where cavity 148 has an inner diameter that less than the outer diameter of the leadless pacing device 10) or simply fit tightly around the leadless pacing device 10 (in the case where cavity 148 has an inner diameter that is substantially the same as the outer diameter of the leadless pacing device 10). The tight dimensional relationship between the leadless pacing device 10 and the distal holding section 146 may provide circumferential frictional engagement between the surfaces 149 and 17, in some cases without applying a compressive force. In some cases, the inner surface 149 of the distal holding section 146, the outer surface 17 of the leadless pacing device 10, or both may include structure, features, or a coating that provides for enhanced frictional engagement between the surfaces 149 and 17.

As can be appreciated, many of these configurations may provide for a delivery device 100 having a smaller or "lower" profile for deliverability purposes. For example, in cases where shrink material or elastic or resilient material are used for the distal holding section 146, all or portions of the holding section 146 can be engineered to have a smaller profile or outer diameter. In some cases, as can be seen in the figures, the distal portion of the holding section 146 (that may extend distally of the leadless pacing device 10 when it is disposed in the cavity) may have a reduced outer diameter. In addition, the tight fit and/or tolerance between the holding section 146 and the device 10 provides for a lower profile.

Referring back to FIG. 3, an example delivery device 100 is shown adjacent a target anatomy (e.g. a portion of the right ventricle RV near the apex of the heart H) with an implantable device 10 disposed in the cavity 148. The distal opening 150 is directed toward the target anatomy, and the distal tip of the delivery device 100 is close to engaging the target anatomy. In this embodiment, the distal holding section 146 may include or be made of a resilient or elastic material or structure that may apply a compressive force to the outer peripheral surface 17 of the leadless pacing device 10 when disposed therein. Such resilient or elastic material or structures may or may not be shrinkable materials, as discussed above. The distal holding section 146 may be dimensioned such that in a relaxed state, the cavity 148 has an inner diameter that is smaller than an outer diameter of the leadless pacing device 10, for example the outer diameter of the housing 12 of the leadless pacing device 10. The leadless pacing device 10 is disposed within the cavity 148, thereby stretching or elastically deforming the distal holding section 146 to receive the leadless pacing device 10. Due to the dimensional differences, and the resilient or elastic properties of the distal holding section 146, a compressive force is applied to the outer peripheral surface 17 of the leadless pacing device 10. As such, in this configuration, with the leadless pacing device 10 disposed in the cavity 148, the distal holding section 146 includes a proximal section 153 having a first inner diameter that is the same as the an outer diameter of the leadless pacing device 10, and a distal section 151 that has a second inner diameter that is less than the outer diameter of the leadless pacing device. Due to the elastic or resilient properties of the distal holding section 146, the distal section 151 may be expandable such that the inner diameter of the distal section 151 will expand as the leadless pacing device 10 is delivered there through.

Figure 4:
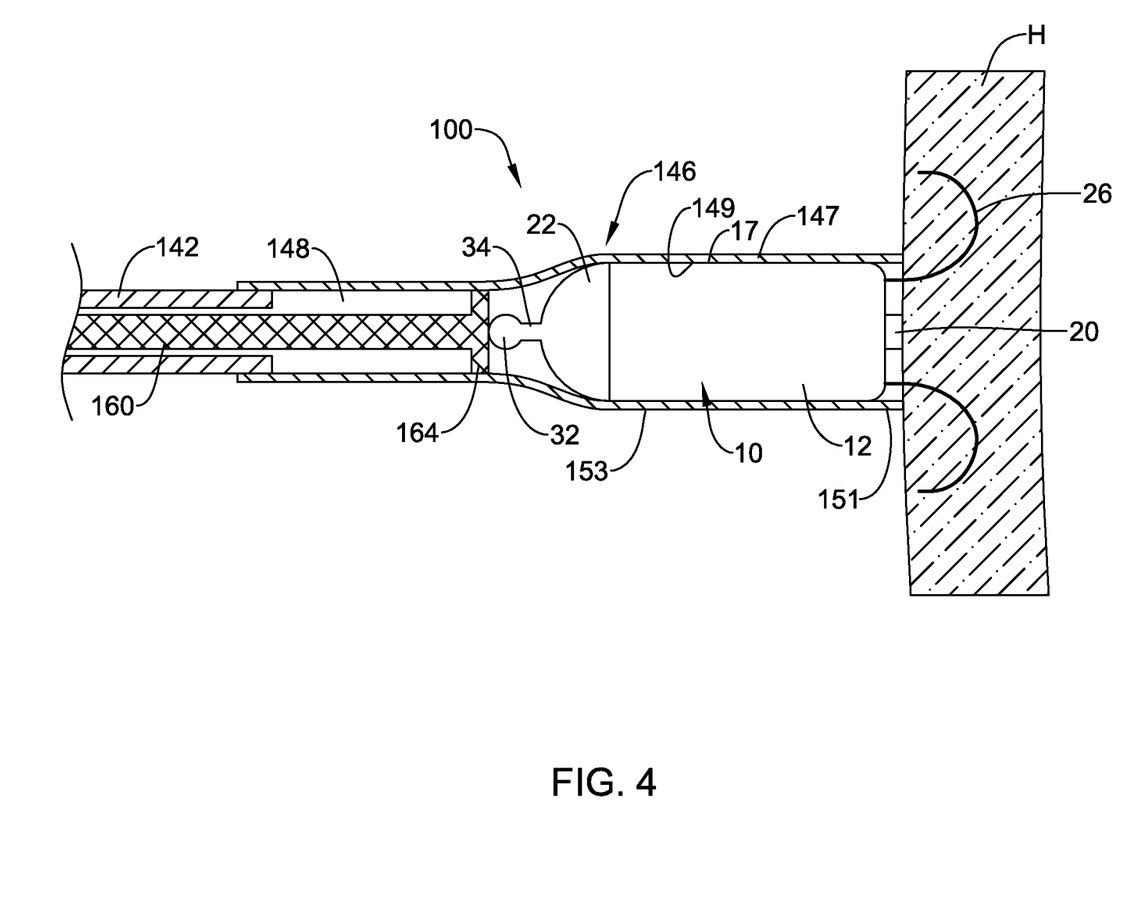
FIG. 4 is a partial cross-sectional side view of the distal portion of the delivery device of FIG. 2, showing the implantable leadless cardiac pacing device disposed therein in a partially deployed configuration.

Moving now to FIG. 4, the system is shown in a partially deployed state. The distal tip of the delivery device 100 is engaging the target anatomy, and the push member 160 has been engaged by a user to engage the device 10, and the push the device 10 distally within the cavity 148. The fixation mechanism (e.g. hooks 26) have anchored into the cardiac tissue of the heart H to attach the implantable device 10 to a tissue wall. As such, in this configuration, due to the elastic nature of the distal holding section 146, the proximal section 153 has relaxed and now has an inner diameter that is less than the outer diameter of the leadless pacing device 10, while the distal section 151 has stretched and now has an inner diameter that is the same as the outer diameter of the leadless pacing device 10.

Figure 5:
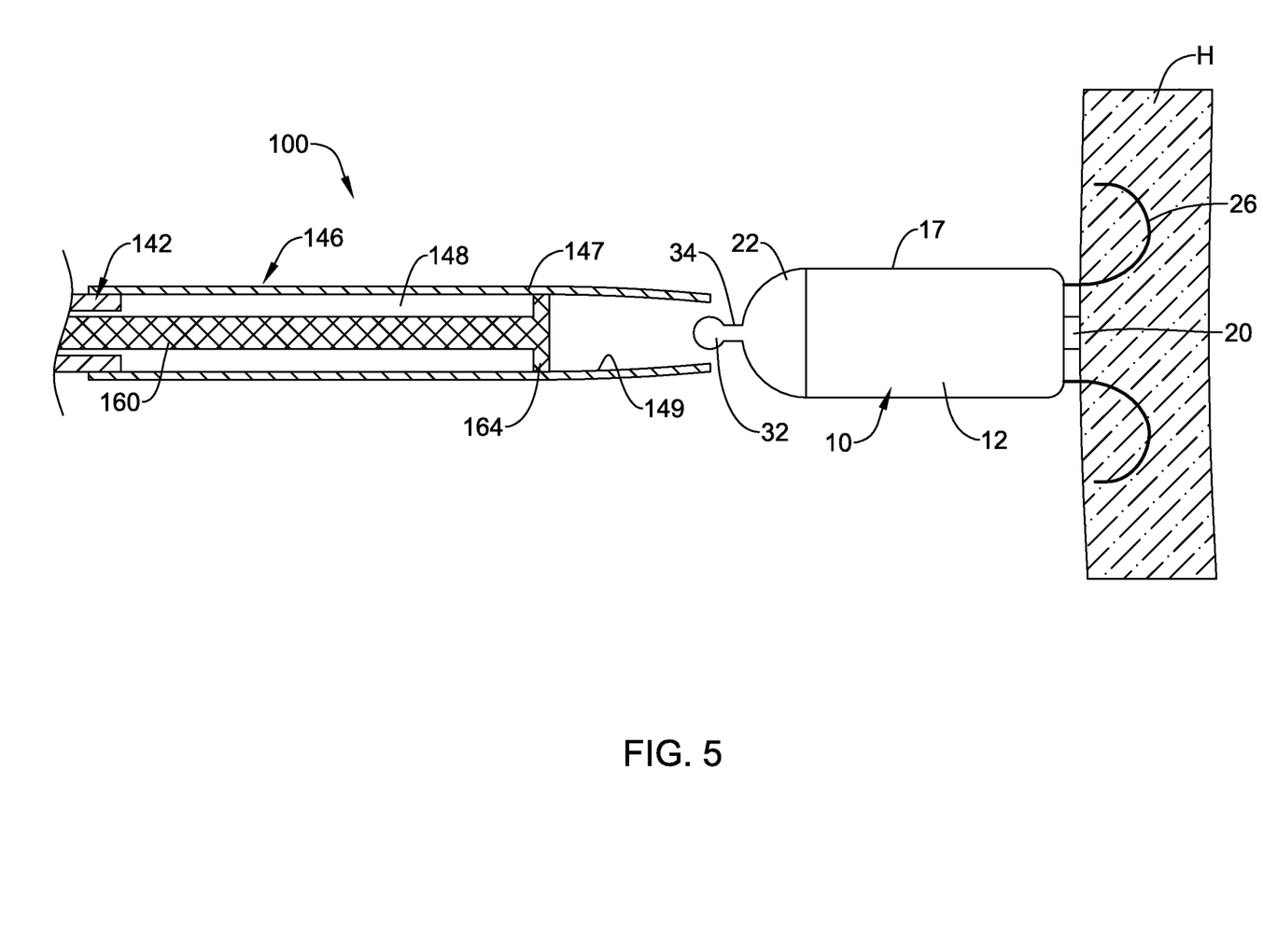
FIG. 5 is a partial cross-sectional side view of the distal portion of the delivery device of FIG. 2, showing the implantable leadless cardiac pacing device deployed therefrom.

Finally, FIG. 5 shows the system after full deployment of the leadless pacing device 10. The leadless pacing device 10 has been pushed fully out of the cavity 148, and is deployed and engaged with the target anatomy. The delivery device 100 has been moved proximally off of the leadless pacing device 10. As such, in this configuration, due to the elastic nature of the distal holding section 146, both the proximal section 153 the distal section 151 of the distal holding section 146 have relaxed, and the entire cavity 148 has an inner diameter that is less than the outer diameter of the leadless pacing device 10. After successful delivery, the delivery device 100 can be withdrawn from the anatomy. It should be understood that the same general procedure may be used for any of the delivery devices and/or systems disclosed herein.

The materials that can be used for the various components of the delivery devices, such as delivery device 100 (or other delivery devices disclosed herein) and the various members disclosed herein may include those commonly associated with medical devices. For simplicity purposes, the following discussion makes reference the delivery devices 100 and components of thereof. However, this is not intended to limit the devices and methods described herein, as the discussion may be applied to other similar delivery systems and/or components of delivery systems or devices disclosed herein.

The delivery device 100 or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about -60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery device 100 or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery devices 100/100b/200/300/400 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

In some embodiments, a degree of Magnetic Resonance Imaging (MRI) compatibility is imparted into the delivery device 100. For example, delivery devices 100/100b/200/300/400, or portions or components thereof, may be made of a material that does not substantially distort the image and create substantial artifacts (i.e., gaps in the image). Certain ferromagnetic materials, for example, may not be suitable because they may create artifacts in an MRI image. The delivery device 100, or portions thereof, may also include and/or be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A delivery system for delivering an implantable leadless pacing device, the delivery system comprising:
    an implantable leadless pacing device including a housing having a proximal end, a distal end, and a cylindrical outer peripheral surface having a constant outer diameter; and
    a delivery device including:
        a proximal section including a distal end,
        a distal holding section extending distally of the distal end of the proximal section, the distal holding section includes an annular wall having an inner surface defining a cavity therein for receiving the implantable leadless pacing device, the distal holding section being configured to apply a compressive force to and conform to the cylindrical outer peripheral surface of the housing of the implantable leadless pacing device when the implantable leadless pacing device is disposed in the cavity,
        wherein the inner surface presses circumferentially against the cylindrical outer peripheral surface of the housing of the implantable leadless pacing device when the implantable leadless pacing device is disposed in the cavity, and
        wherein there is no gap or opening between the inner surface of the distal holding section and an entirety of the cylindrical outer peripheral surface of the housing;
        wherein when the implantable leadless pacing device is fully disposed in the cavity, the distal holding section includes a distally facing opening distal of the cylindrical outer peripheral surface of the housing of the implantable leadless pacing device, the distal opening having an inner diameter that is less than the outer diameter of the cylindrical outer peripheral surface of the housing of the implantable leadless pacing device;
        wherein the distal opening is configured to expand as the housing of the implantable leadless pacing device passes therethrough.

2. The delivery system of claim 1, wherein the distal holding section comprises a resilient material that applies the compressive force to the cylindrical outer peripheral surface of the housing of the implantable leadless pacing device.

3. The delivery system of claim 1, wherein the distal holding section comprises a resilient material that elastically deforms when the implantable leadless pacing device is disposed in the cavity.

4. The delivery system of claim 1, wherein the cavity of the distal holding section comprises an inner diameter, and the inner diameter of the cavity is the same as or less than the outer diameter of the cylindrical outer peripheral surface of the housing of the implantable leadless pacing device when the implantable leadless pacing device is disposed outside of the cavity.

5. The delivery system of claim 4, wherein the inner diameter of the cavity is less than the outer diameter of the cylindrical outer peripheral surface of the housing of the implantable leadless pacing device, and the distal holding section is expandable such that the inner diameter of the cavity expands when the implantable leadless pacing device is disposed in the cavity.

6. The delivery system of claim 1, wherein the cavity of the distal holding section comprises a distal portion extending distal of the cylindrical outer peripheral surface of the housing of the implantable leadless pacing device that has an inner diameter that is less than the outer diameter of the cylindrical outer peripheral surface of the housing of the implantable leadless pacing device when the implantable leadless pacing device is disposed in the cavity;
    wherein the distal portion is expandable such that the inner diameter of the distal portion will expand as the implantable leadless pacing device is delivered therethrough.

7. The delivery system of claim 1, wherein the cavity of the distal holding section includes a proximal section having a first inner diameter that is the same as the outer diameter of the cylindrical outer peripheral surface of the housing of the implantable leadless pacing device, and a distal section that has a second inner diameter that is less than the outer diameter of the cylindrical outer peripheral surface of the housing of the implantable leadless pacing device.

8. The delivery system of claim 1, wherein the compressive force applied by the distal holding section to the cylindrical outer peripheral surface of the housing of the implantable leadless pacing device provides circumferential frictional engagement between the distal holding section and the housing of the implantable leadless pacing device.

9. The delivery system of claim 1, wherein when the housing of the implantable leadless pacing device is disposed outside of the distal holding section, the cavity of the distal holding section includes:
    a proximal portion having a first inner diameter that is less than the outer diameter of the cylindrical outer peripheral surface of the housing of the implantable leadless pacing device, and
    a distal portion that has a second inner diameter at a distal end of the distal portion that is less than the first inner diameter;
    wherein the proximal portion is configured to radially expand to a third inner diameter greater than the first inner diameter when the housing of the implantable leadless pacing device is disposed therein;
    wherein the distal portion is configured to radially expand to the third inner diameter when the housing of the implantable leadless pacing device passes therethrough;

wherein the distal portion is configured to radially contract to a fourth inner diameter less than the third inner diameter when the implantable leadless pacing device is disposed in the proximal portion.

10. A delivery system for delivering an implantable leadless pacing device, the delivery system comprising:
an implantable leadless pacing device including:
a housing including electrical circuitry therein, the housing having a cylindrical outer peripheral surface having a constant outer diameter; and
a fixation mechanism disposed at a distal end of the housing;
a delivery device including:
a proximal section including a distal end, and
a distal holding section extending distally of a distal end of the proximal section, the distal holding section includes an annular wall having an inner surface defining a cavity therein for receiving the implantable leadless pacing device, the distal holding section being configured to conform to the cylindrical outer peripheral surface of the housing of the implantable leadless pacing device when the implantable leadless pacing device is disposed in the cavity to provide circumferential frictional engagement with the cylindrical outer peripheral surface of the housing of the implantable leadless pacing device,
wherein the inner surface circumferentially frictionally engages the cylindrical outer peripheral surface of the housing of the implantable leadless pacing device when the implantable leadless pacing device is disposed in the cavity while being free of any gap between the inner surface and the cylindrical outer peripheral surface of the housing.

11. The delivery system of claim 10, wherein the cavity of the distal holding section is radially expanded when the distal holding section receives the implantable leadless pacing device therein.

12. The delivery system of claim 10, wherein a distal portion of the distal holding section extending distal of the cylindrical outer peripheral surface of the housing of the implantable leadless pacing device has an inner diameter less than the outer diameter of the cylindrical outer peripheral surface of the housing when the implantable leadless pacing device is disposed in the cavity.

13. The delivery system of claim 12, wherein the distal portion is expandable such that the inner diameter of the distal portion expands as the housing of the implantable leadless pacing device passes therethrough.

14. The delivery system of claim 10, wherein the distal holding section includes a distal opening at a distal extremity thereof opening into the cavity, the distal opening having a radially collapsed diameter less than the outer diameter of the cylindrical outer peripheral surface of the housing when the implantable leadless pacing device is fully disposed in the cavity, and the distal opening having a radially expanded diameter equal to the outer diameter of the cylindrical outer peripheral surface of the housing as the housing of the implantable leadless pacing device passes through the distal opening.

15. The delivery system of claim 10, wherein the distal holding section includes a proximal portion and a distal portion located distal of the proximal portion, the proximal portion of the distal holding section circumferentially surrounding the cylindrical outer peripheral surface of the housing when the implantable leadless pacing device is fully disposed in the cavity and the distal portion of the distal holding section circumferentially surrounding the fixation mechanism when the implantable leadless pacing device is fully disposed in the cavity,
wherein the proximal portion of the distal holding section has an inner diameter equal to the outer diameter of the cylindrical outer peripheral surface of the housing when the implantable leadless pacing device is fully disposed in the cavity, and the distal portion of the distal holding section has an inner diameter less than the inner diameter of the proximal portion of the distal holding section when the implantable leadless pacing device is fully disposed in the cavity.

16. The delivery system of claim 15, wherein the distal portion of the distal holding section gradually tapers down to a smaller diameter in a distal direction from the proximal portion of the distal holding section to a distal extremity of the distal holding section.

17. The delivery system of claim 15, wherein the distal holding section includes a distal opening at a distal extremity thereof opening into the cavity, the distal opening having a radially collapsed diameter less than the inner diameter of the proximal portion of the distal holding section when the implantable leadless pacing device is fully disposed in the cavity, and the distal opening having a radially expanded diameter equal to the inner diameter of the proximal portion of the distal holding section as the implantable leadless pacing device is deployed out through the distal opening.

18. A delivery system for delivering an implantable leadless pacing device, the delivery system comprising:
an implantable leadless pacing device including a housing having a cylindrical outer peripheral surface having a constant outer diameter; and
a delivery device including:
a proximal section including a distal end, and
a distal holding section extending distally of the distal end of the proximal section, the distal holding section includes an annular wall having an inner surface defining a cavity therein for receiving the implantable leadless pacing device, the distal holding section having an inner diameter in a relaxed state less than the outer diameter of the housing of the implantable leadless pacing device such that the distal holding section radially expands to engage an entirety of the cylindrical outer peripheral surface of the housing of the implantable leadless pacing device around an entire circumference of the housing of the implantable leadless pacing device when the implantable leadless pacing device is disposed in the cavity while being free of any gap between the inner surface and the cylindrical outer peripheral surface of the housing;
wherein a distal end of the distal holding section defines a distal opening coaxial with and opening into the cavity of the distal holding section, the distal opening having an inner diameter less than the outer diameter of the housing of the implantable leadless pacing device when the implantable leadless pacing device is fully disposed in the cavity.

19. The delivery system of claim 18, wherein a distal section of the distal holding section extending distal of the cylindrical outer peripheral surface of the housing of the implantable leadless pacing device has an inner diameter less than the outer diameter of the housing when the implantable leadless pacing device is disposed in the cavity.

20. The delivery system of claim 19, wherein the distal section is expandable such that the inner diameter of the distal section expands as the housing of the implantable leadless pacing device passes therethrough.

* * * * *